(12) United States Patent
Kim et al.

(10) Patent No.: US 10,129,926 B2
(45) Date of Patent: Nov. 13, 2018

(54) WIRELESS COMMUNICATION METHOD OF PROBE FOR ULTRASOUND DIAGNOSIS AND APPARATUS THEREFOR

(75) Inventors: Kang-sik Kim, Gyeonggi-do (KR); Soon-jae Hong, Gyeonggi-do (KR); Jung-jun Kim, Seoul (KR); Ho-san Han, Seoul (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 297 days.

(21) Appl. No.: 13/495,364

(22) Filed: Jun. 13, 2012

(65) Prior Publication Data

US 2013/0028153 A1 Jan. 31, 2013

(30) Foreign Application Priority Data

Jul. 25, 2011 (KR) .......................... 10-2011-0073773

(51) Int. Cl.
*H04W 84/12* (2009.01)
*A61B 8/00* (2006.01)

(52) U.S. Cl.
CPC .......... *H04W 84/12* (2013.01); *A61B 8/4472* (2013.01); *A61B 8/4405* (2013.01)

(58) Field of Classification Search
None
See application file for complete search history.

(56) References Cited

U.S. PATENT DOCUMENTS

| 7,346,364 | B1 * | 3/2008 | Tsien | H04W 52/267 370/318 |
| 2004/0015079 | A1 * | 1/2004 | Berger et al. | 600/437 |
| 2006/0105712 | A1 * | 5/2006 | Glass | G06F 21/31 455/41.2 |
| 2008/0026745 | A1 * | 1/2008 | Grubb | H04W 8/245 455/426.1 |
| 2008/0310354 | A1 * | 12/2008 | Hansen | H04W 72/04 370/329 |

(Continued)

FOREIGN PATENT DOCUMENTS

| CN | 101352334 A | 1/2009 |
| CN | 101919708 A | 12/2010 |

(Continued)

OTHER PUBLICATIONS

WiGig White Paper: Defining the Future of Multi-Gigabit Wireless Communications, WiGig White Paper, Wireless Gigabit Alliance, US, Jul. 1, 2010, pp. 1-5, XP008173868, http://wirelessgigabitalliance.org.

(Continued)

*Primary Examiner* — Chirag G Shah
*Assistant Examiner* — Suk Jin Kang
(74) *Attorney, Agent, or Firm* — Cha + Reiter, LLC.

(57) ABSTRACT

A probe apparatus for ultrasound diagnostic imaging associates with a mmWave-based Personal Basic Service Set (PBSS), performs pairing with an ultrasonic imaging apparatus, and transmits an echo signal received via a transducer portion of the probe, to the ultrasonic imaging apparatus using a signal channel in a 60 GHz frequency band, thereby obviating the need for a data transmission cable and greatly reducing operator inconvenience.

22 Claims, 12 Drawing Sheets

(56) References Cited

U.S. PATENT DOCUMENTS

| | | | |
|---|---|---|---|
| 2009/0006677 A1* | 1/2009 | Rofougaran | H01Q 1/2275 710/63 |
| 2010/0144285 A1* | 6/2010 | Behzad | H04B 1/40 455/73 |
| 2010/0160784 A1 | 6/2010 | Poland et al. | |
| 2010/0160786 A1* | 6/2010 | Nordgren et al. | 600/459 |
| 2010/0168576 A1* | 7/2010 | Poland et al. | 600/443 |
| 2010/0191121 A1* | 7/2010 | Satoh et al. | 600/459 |
| 2010/0262696 A1* | 10/2010 | Oshiba | H04M 1/7253 709/227 |
| 2010/0286527 A1* | 11/2010 | Cannon | A61B 7/04 600/459 |
| 2010/0298711 A1* | 11/2010 | Pedersen | A61B 8/00 600/459 |
| 2011/0105904 A1 | 5/2011 | Watanabe | |
| 2011/0119745 A1* | 5/2011 | Bremner | H04L 63/0853 726/7 |
| 2011/0143665 A1* | 6/2011 | Cordeiro et al. | 455/41.2 |
| 2011/0154039 A1* | 6/2011 | Liu | H04L 63/0869 713/170 |
| 2011/0158145 A1* | 6/2011 | Gong | H04L 12/185 370/312 |
| 2011/0171914 A1* | 7/2011 | Kim | H04L 1/0026 455/68 |
| 2011/0182333 A1* | 7/2011 | Rofougaran | H04B 1/3805 375/220 |
| 2011/0195665 A1* | 8/2011 | Friedlaender | G08C 17/02 455/41.2 |
| 2011/0207460 A1 | 8/2011 | Kim et al. | |
| 2011/0245671 A1* | 10/2011 | Sato | 600/443 |
| 2012/0044057 A1* | 2/2012 | Kang | H04L 63/10 340/10.4 |
| 2012/0051355 A1* | 3/2012 | Rofougaran | H04W 74/0808 370/342 |
| 2012/0057580 A1* | 3/2012 | Hansen | G01S 1/02 370/338 |
| 2012/0177016 A1* | 7/2012 | Trainin et al. | 370/338 |
| 2012/0182893 A1* | 7/2012 | Trainin et al. | 370/252 |
| 2012/0197127 A1* | 8/2012 | Nakamura et al. | 600/447 |
| 2012/0294339 A1* | 11/2012 | Rofougaran | G06K 7/0008 375/219 |
| 2013/0003568 A1* | 1/2013 | Xie | H04L 27/2659 370/252 |
| 2013/0003662 A1* | 1/2013 | Lee | H04W 74/06 370/329 |
| 2013/0003709 A1* | 1/2013 | Kalhan | H04W 76/025 370/338 |
| 2013/0163496 A1* | 6/2013 | Trainin | H04L 61/6022 370/311 |
| 2014/0011445 A1* | 1/2014 | Trainin | H04W 24/00 455/39 |
| 2014/0162569 A1* | 6/2014 | Kim | H04L 1/0026 455/69 |
| 2015/0156732 A1* | 6/2015 | Trainin | H04W 52/245 370/329 |
| 2016/0227450 A1 | 8/2016 | Son et al. | |

FOREIGN PATENT DOCUMENTS

| | | |
|---|---|---|
| CN | 102076264 A | 5/2011 |
| JP | 2007-282957 A | 11/2007 |
| KR | 10-2008-0090957 A | 10/2008 |
| KR | 10-2011-0035969 A | 4/2011 |
| KR | 10-2011-0097571 A1 | 8/2011 |
| RU | 2 386 389 C2 | 3/2008 |
| WO | 2008/115312 A2 | 9/2008 |
| WO | 2008/146204 A2 | 12/2008 |
| WO | 2011/087210 A2 | 7/2011 |

OTHER PUBLICATIONS

Japanese Search Report dated Jun. 27, 2016.
Korean Search Report dated Oct. 18, 2016.
European Search Report dated Feb. 16, 2017.
Russian Search Report dated Mar. 24, 2017.

* cited by examiner

WIRELESS COMMUNICATION METHOD OF PROBE FOR ULTRASOUND DIAGNOSIS AND APPARATUS THEREFOR

CLAIM OF PRIORITY

This application claims priority under 35 U.S.C. § 119(a) of the earlier filing date of Korean Patent Application No. 10-2011-0073773, filed on Jul. 25, 2011, in the Korean Intellectual Property Office, the entire disclosure of which is incorporated herein by reference.

BACKGROUND OF THE INVENTION

1. Field of the Invention

The present invention relates to a method in which a probe apparatus for ultrasound diagnosis transmits an echo signal to an ultrasonic imaging apparatus, and an apparatus for performing the method.

2. Description of the Related Art

Ultrasound diagnostic imaging systems transmit ultrasonic signals from the surface of a human body toward a predetermined region inside the human body and acquire tomographic images of soft-tissue or blood flow by using information obtained from an ultrasonic signal reflected by liquids or tissue inside the human body. Advantages of an ultrasound system are its relatively small size, low cost, real-time display, and the fact that the subject is not exposed to ionizing radiation (e.g., X-rays). Therefore, ultrasound imaging systems are widely used along with other types of image diagnostic devices, such as an X-ray diagnostic device, a computerized tomography (CT) scanner, a magnetic resonance imaging (MRI) device, a nuclear medicine (gamma camera) diagnostic device, etc.

FIG. 1 illustrates a typical ultrasound diagnostic imaging system 150 as currently in use today, which diagnostic includes a probe 110 for transceiving ultrasonic signals, and an ultrasound diagnostic imaging system body 100, namely, an ultrasonic imaging apparatus 100, to which the probe 110 is connected via a cable 120. However, the cable 120 causes much inconvenience to a person using the ultrasound imaging system 150 to perform an ultrasound test, due to the length (usually 1-2 m), thickness and weight of the cable 120.

SUMMARY OF THE INVENTION

The present invention provides a method and apparatus for wirelessly transmitting an echo signal to an ultrasonic imaging apparatus without loss.

According to an aspect of the present invention, there is provided a probe apparatus for ultrasound diagnostic imaging, the probe apparatus comprising: an association performing unit which performs a procedure for associating the probe apparatus with a mmWave-based wireless network; a frame generation unit which generates a data frame with a format suitable for the mmWave-based wireless network, by using an echo signal received via a transducer; and a wireless communication unit which transmits the data frame to an ultrasonic imaging apparatus using a signal channel in a 60 GHz frequency band via the mmWave-based wireless network.

The mmWave-based wireless network may be a Personal Basic Service Set (PBSS) that follows the WiGig standard of the Wireless Gigabit Alliance (WGA), and the ultrasonic imaging apparatus operates as a PBSS control point (PCP) of the PBSS.

The probe apparatus may further include a beam forming unit which performs mmWave beamforming of the signal in the 60 GHz frequency band in order to transmit the data frame to the ultrasonic imaging apparatus.

According to another aspect of the present invention, there is provided a probe apparatus for ultrasound diagnostic imaging, the probe apparatus comprising: a beacon monitoring unit which monitors for the reception of a mmWave beacon from an ultrasonic imaging apparatus of a Personal Basic Service Set (PBSS) with which the probe apparatus is not yet associated, when a user command for making a pairing request is received; a peer determination unit which detects an ultrasonic imaging apparatus which is to be paired with the probe apparatus by using first pairing information included in a received mmWave beacon; an association performing unit which performs a procedure for associating the probe apparatus with a PBSS of the ultrasonic imaging apparatus by using a basic service set ID (BSSID) included in the received mmWave beacon; and a pairing request unit which transmits second pairing information to the ultrasonic imaging apparatus via the PBSS, wherein the first pairing information represents that the ultrasonic imaging apparatus has been requested by a user to perform pairing, and the second pairing information represents that the probe apparatus has been requested by the user to perform pairing.

The first pairing information may comprise a medium access control (MAC) address of the ultrasonic imaging apparatus and push button configuration (PBC) information representing that a button for requesting pairing by using a PBC technique has been pressed in the ultrasonic imaging apparatus, and the second pairing information comprises a MAC address of the probe apparatus and PBC information representing that a button for requesting pairing by using the PBC technique has been pressed in the probe apparatus.

The probe apparatus may further comprise a wireless communication unit which transmits an echo signal received via a transducer portion of the probe, to the ultrasonic imaging apparatus via a signal channel in a 60 GHz frequency band via the PBSS of the ultrasonic imaging apparatus.

The probe apparatus may further comprise a beam forming unit which performs mmWave beamforming with the ultrasonic imaging apparatus.

According to another aspect of the present invention, there is provided a probe apparatus for ultrasound diagnostic imaging, the probe apparatus comprising: a link formation unit which forms a communication link with an ultrasonic imaging apparatus in a PBSS that uses mmWaves; a margin information processing unit which extracts information about a link margin of the communication link from a link margin response frame received from the ultrasonic imaging apparatus; and a margin control unit which controls the probe apparatus to perform at least one of a change in transmission power of an echo signal, a change in a modulation and coding scheme (MCS) to be applied to the echo signal, a change in beam forming with the ultrasonic imaging apparatus, and a change in channel frequency within a 60 GHz frequency band based on the information.

The margin information processing unit may transmit a link margin request frame requesting information about the link margin to the ultrasonic imaging apparatus, and the link margin response frame may be received in response to the link margin request frame.

The link margin request frame may comprise at least one of a category field indicating what kind of frame the link margin request frame belongs to, an action field indicating that the link margin response frame is a link margin request frame from among frames categorized into the kind of frame determined by the category field, and a transmission number field representing the number of times the link margin request frame is transmitted.

The link margin response frame may comprise a preferred action field that comprises information that indicates a request for one operation from among the change in the transmission power, the change in the MCS, the change in beam forming, and the change in channels, to be performed.

According to another aspect of the present invention, there is provided an ultrasound diagnostic system comprising: a probe apparatus which is associated with a mmWave-based wireless network, which probe apparatus transmits an echo signal received via a transducer portion of the probe apparatus to an ultrasonic imaging apparatus using a signal channel in a 60 GHz frequency band via the mmWave-based wireless network; and the ultrasonic imaging apparatus which generates an ultrasonic image by using the echo signal received in the 60 GHz frequency band via the mmWave-based wireless network.

The mmWave-based wireless network may be a personal basic service set (PBSS) that follows the WiGig standard of the Wireless Gigabit Alliance (WGA), and the ultrasonic imaging apparatus operates as a PBSS control point (PCP) of the PBSS.

BRIEF DESCRIPTION OF THE DRAWINGS

The above and other features and advantages of the present invention will become more apparent by describing in detail exemplary embodiments thereof with reference to the attached drawings in which.

Throughout the drawings, the same drawing reference numerals will be understood to refer to the same elements, features and structures.

DETAILED DESCRIPTION

The following description, with reference to the accompanying drawings, is provided to assist a person of ordinary skill in the art with a comprehensive understanding of exemplary embodiments of the invention. The description includes various specific details to assist in that understanding but these details are to be regarded as merely exemplary. Accordingly, those of ordinary skill in the art will recognize that various changes and modifications of the exemplary embodiments described herein can be made without departing from the spirit of the invention and the scope of the appended claims. Also, descriptions of well-known functions and constructions may be omitted for clarity and simplicity so as not to obscure appreciation of the present invention by a person of ordinary skill with such well-known functions and constructions.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention are provided for illustration purposes only and not for the purpose of limiting the invention as defined by the appended claims.

Expressions such as "at least one of," when preceding a list of elements, refers to at least one of the entire list of elements and is not intended to be limited individual elements of the list.

It is to be understood that the singular forms "a", "an", and "the" include plural references unless the context clearly dictates otherwise. Thus, for example, reference to "a component surface" typically includes reference to one or more of such surfaces.

Finally, the term "substantially" typically means that the recited characteristic, parameter, or value need not be achieved exactly, but that deviations or variations, including for example, tolerances, measurement error, measurement accuracy limitations and other factors known to those skilled in the art, may occur in amounts that do not preclude the effect the characteristic was intended to provide.

Figure 1:
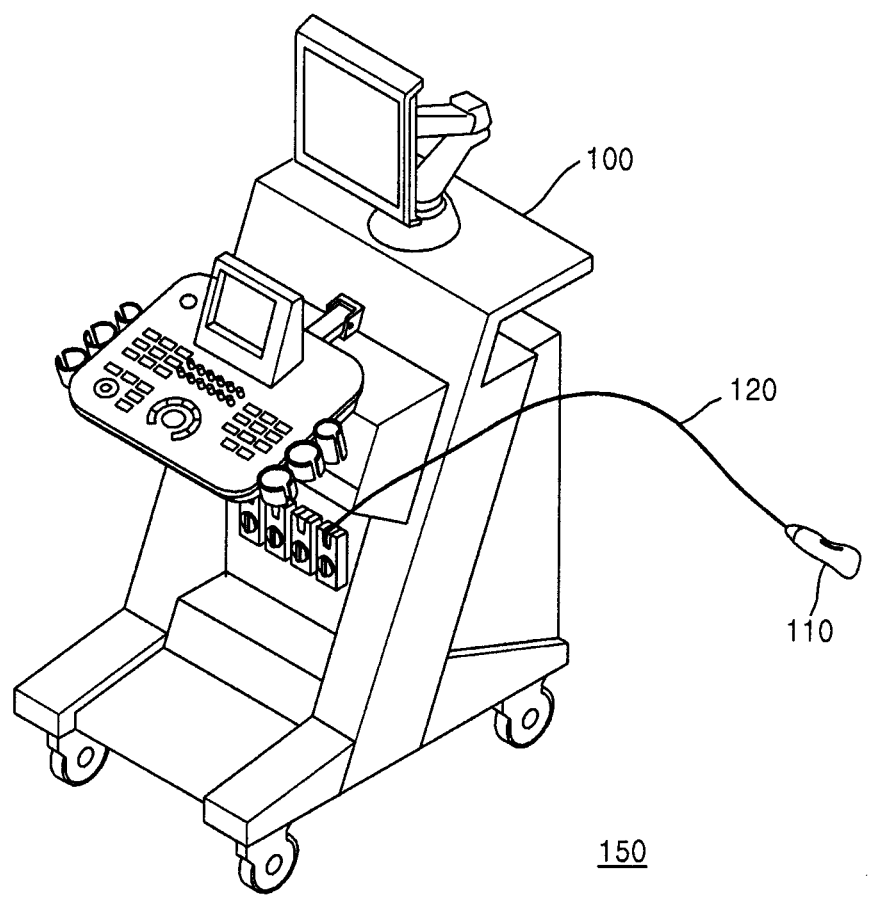
FIG. 1 illustrates a prior art ultrasound diagnostic imaging system.
Figure 2:
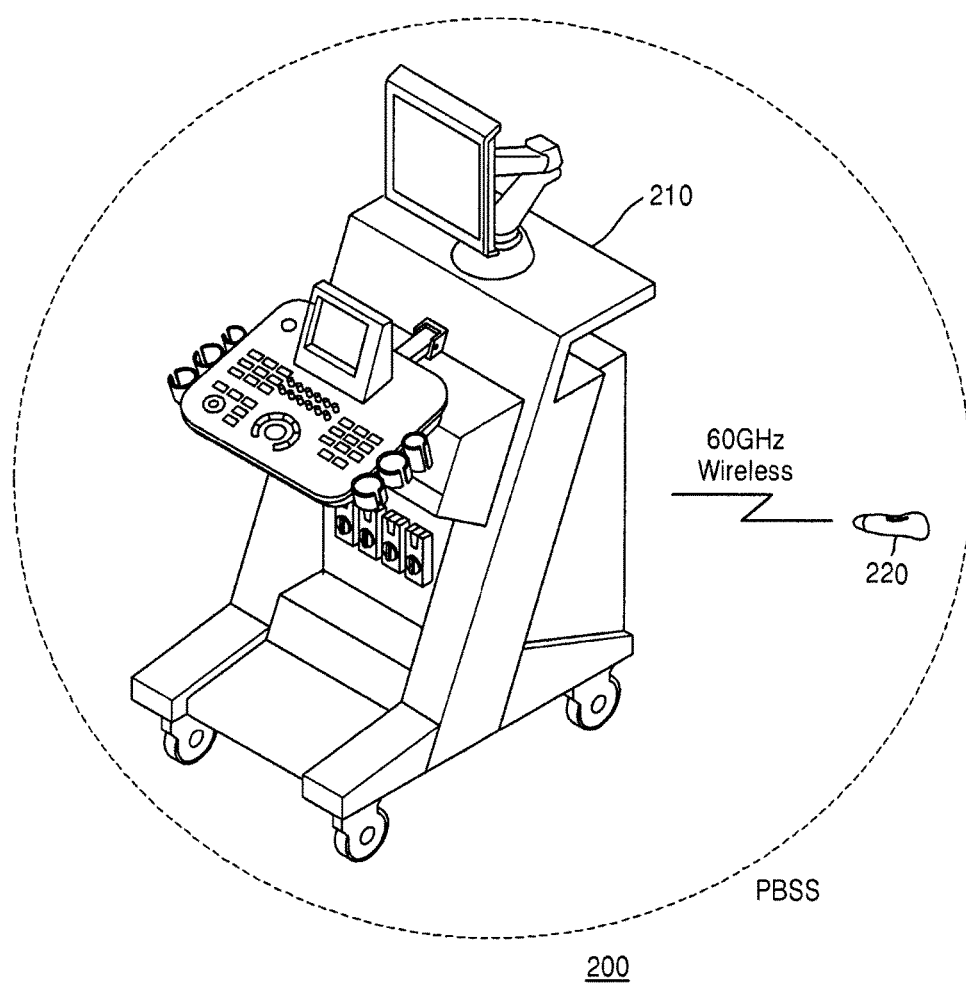
FIG. 2 illustrates an ultrasound diagnostic imaging system according to an embodiment of the present invention.

FIG. 2 illustrates an ultrasound diagnostic imaging system 200 according to an embodiment of the present invention, which diagnostic includes an ultrasonic imaging apparatus 210 and a probe 220 including an ultrasonic wave transducer. The probe 220 and the ultrasonic imaging apparatus 210 are associated with a same mmWave (millimeter Wave)-based wireless network, and the probe 220 transmits an echo signal received via the transducer portion of the probe, to the ultrasonic imaging apparatus 210 using one or more signal channels in the 60 GHz frequency band. The ultrasonic imaging apparatus 210 generates ultrasonic images in various modes, such as B-mode, color flow, and Doppler, by using the ultrasound echo signal transmitted thereto using the 60 GHz frequency band signal channel, and displays the ultrasonic images.

The probe 220 generates an ultrasonic signal by applying one or more pulses to an ultrasonic oscillator of a transducer. Once generated, the ultrasonic signal is reflected by a target (such as structures in a human body) and is received as an echo signal by the transducer. The transducer converts the echo signal into an electrical signal, and then requires a high bandwidth communication channel on the order of multiple gigabytes, to wirelessly transmit the electrical signal, and also so as to not interfere with other wireless electronic apparatuses during wireless transmission of the echo signal.

To this end, according to embodiments of the present invention, an echo signal is wirelessly transmitted via a wireless network that uses millimeter waves. For example, a wireless communication technique based on the WiGig standard of the Wireless Gigabit Alliance (WGA) may be used.

The WiGig standard is sufficient to transmit an echo signal that has been converted into digital data because the WiGig standard supports data transmission rates up to 7 Gbps, and may steer a signal direction by using the directionality of beams to minimize interference with other systems. The WiGig standard as a local-distance wireless communication standard is also generally suitable for ultrasonic test environments where a probe and an ultrasonic imaging apparatus are close to each other, and using the WiGig standard consumes less power than other wireless communication standards and thus may minimize the weight and size of battery which is to be built into the probe. The dashed line circle in FIG. 2 enclosing probe 220 and the ultrasonic imaging apparatus 210 denotes a wireless communication network with which the probe and imaging apparatus communicate with each other, and may be a personal basic service set (PBSS) of the WiGig standard, as explained in more detail below.

Figure 3:
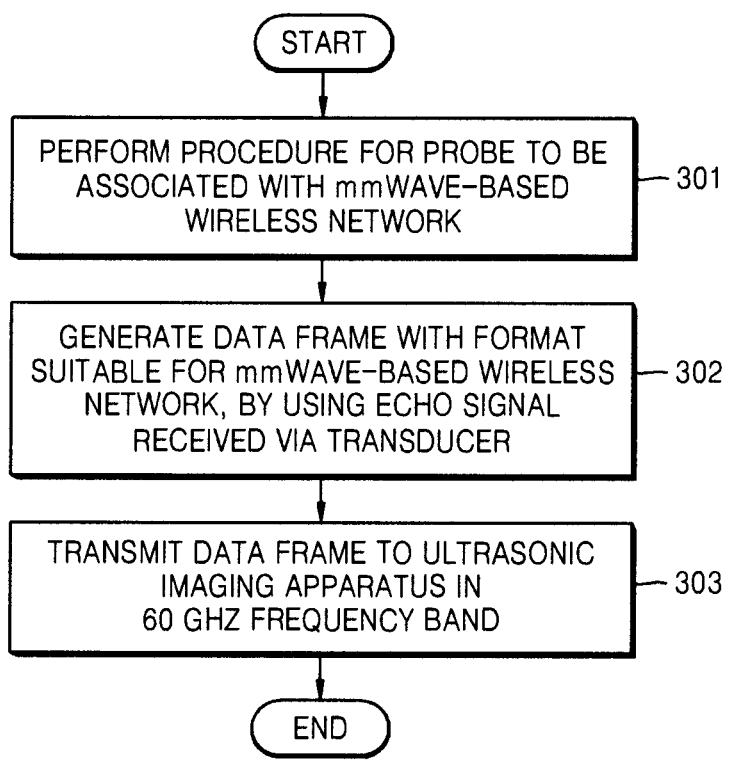
FIG. 3 is a flowchart illustrating a communication process of a probe, according to an embodiment of the present invention.

FIG. 3 is a flowchart of a communication process performed by a probe, according to an embodiment of the present invention.

In operation 301, the probe performs a procedure in order to become associated with a PBSS mmWave-based wireless network. In the PBSS, at least one station needs to operate as a PBSS control point (PCP) that manages the PBSS. However, the probe is limited in its size and weight, and thus it may be preferred that the ultrasonic imaging apparatus 210 may operate as the PCP. Alternatively, both the ultrasonic imaging apparatus and the probe may operate as a station, and another device may operate as the PCP in the PBSS.

In operation 302, the probe generates a data frame with a format suitable for the mmWave-based wireless network, by using an echo signal received via the transducer.

In operation 303, the probe transmits the data frame to the ultrasonic imaging apparatus using a signal in a 60 GHz frequency band. The ultrasonic imaging apparatus (such as 210 of FIG. 2) receives the data frame, generates therefrom an ultrasonic image via signal processing, and displays the ultrasonic image.

Figure 4:
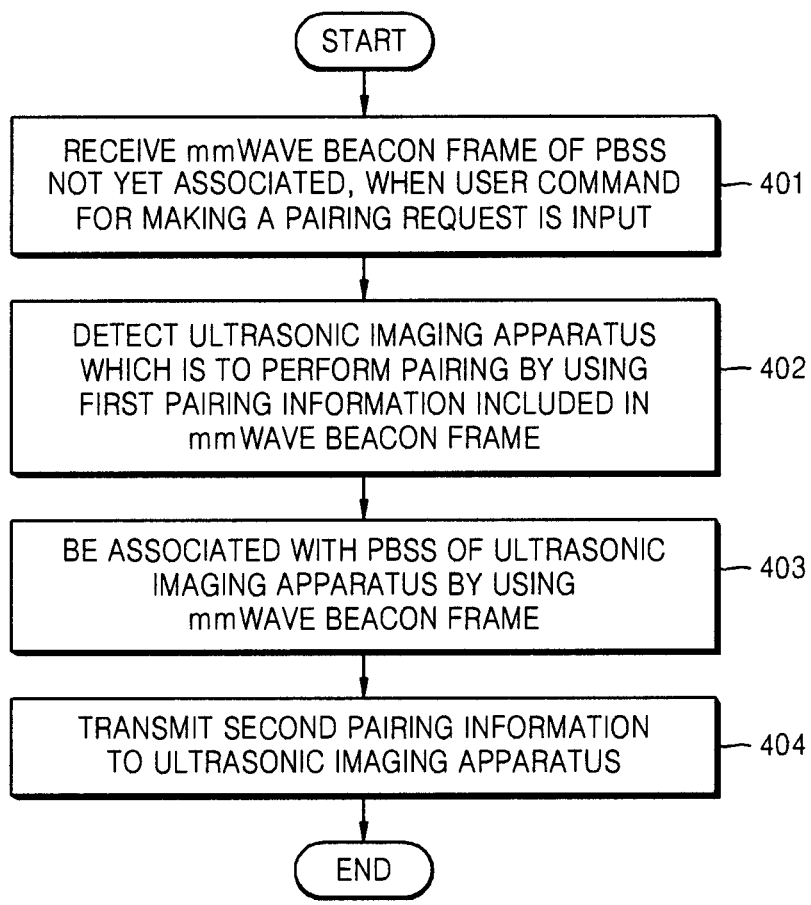
FIG. 4 is a flowchart illustrating a process in which the probe performs pairing with an ultrasonic imaging apparatus, according to an embodiment of the present invention.

FIG. 4 is a flowchart of a process in which the probe performs pairing with the ultrasonic imaging apparatus, according to an embodiment of the present invention.

The PBSS is an ad-hoc structure that performs direct communication between stations without passing through a PCP. Accordingly, the probe and the ultrasonic imaging apparatus need to be subjected to a process of recognizing themselves as peer devices and setting a communication protocol to perform mutual communication. This process is referred to as pairing. A push button configuration (PBC) method may be used to perform pairing between the probe and the ultrasonic imaging apparatus. In other words, when a user pushes pairing buttons included in the probe and the ultrasonic imaging apparatus simultaneously (or within a short time interval therebetween), the probe and the ultrasonic imaging apparatus are paired.

In operation 401, when a user command for making a pairing request is input, that is, when a pairing button is pressed, the probe receives a mmWave beacon frame (hereinafter, referred to as a beacon frame) of the PBSS not yet associated. Before the user command for making a pairing request is input, the probe is not associated with the PBSS of the ultrasonic imaging apparatus, and thus does not parse a beacon frame broadcast from the PBSS to which the ultrasonic imaging apparatus belongs, but discards it. However, when a user presses the pairing buttons, the probe starts monitoring an externally received beacon frame.

In operation 402, the probe detects the ultrasonic imaging apparatus which is to be paired with the probe by using first pairing information included in the beacon frame. It is assumed that the ultrasonic imaging apparatus has already belonged to the PBSS, and the ultrasonic imaging apparatus may operate as a PCP or a general station rather than the PCP in the PBSS. When a user presses the pairing button included in the ultrasonic imaging apparatus to perform pairing, the PCP of the PBSS broadcasts the first pairing information, representing that the ultrasonic imaging apparatus has requested pairing, via a beacon frame. The first pairing information may include PBC information representing that the pairing button of the ultrasonic imaging apparatus has been pressed, and a medium access control (MAC) address of the ultrasonic imaging apparatus.

In operation 403, the probe is associated with the PBSS of the ultrasonic imaging apparatus by using Basic Service Set ID (BSSID) included in the beacon frame. Although the probe is associated with the PBSS after determining a peer device (operation 402) in the present embodiment, operation 403 may be performed before operation 402.

In operation 404, the probe transmits second pairing information to the ultrasonic imaging apparatus. The second pairing information represents that the probe has requested pairing, and may include PBC information representing that the pairing button of the probe has been pressed, and a MAC address of the probe.

Figure 5:
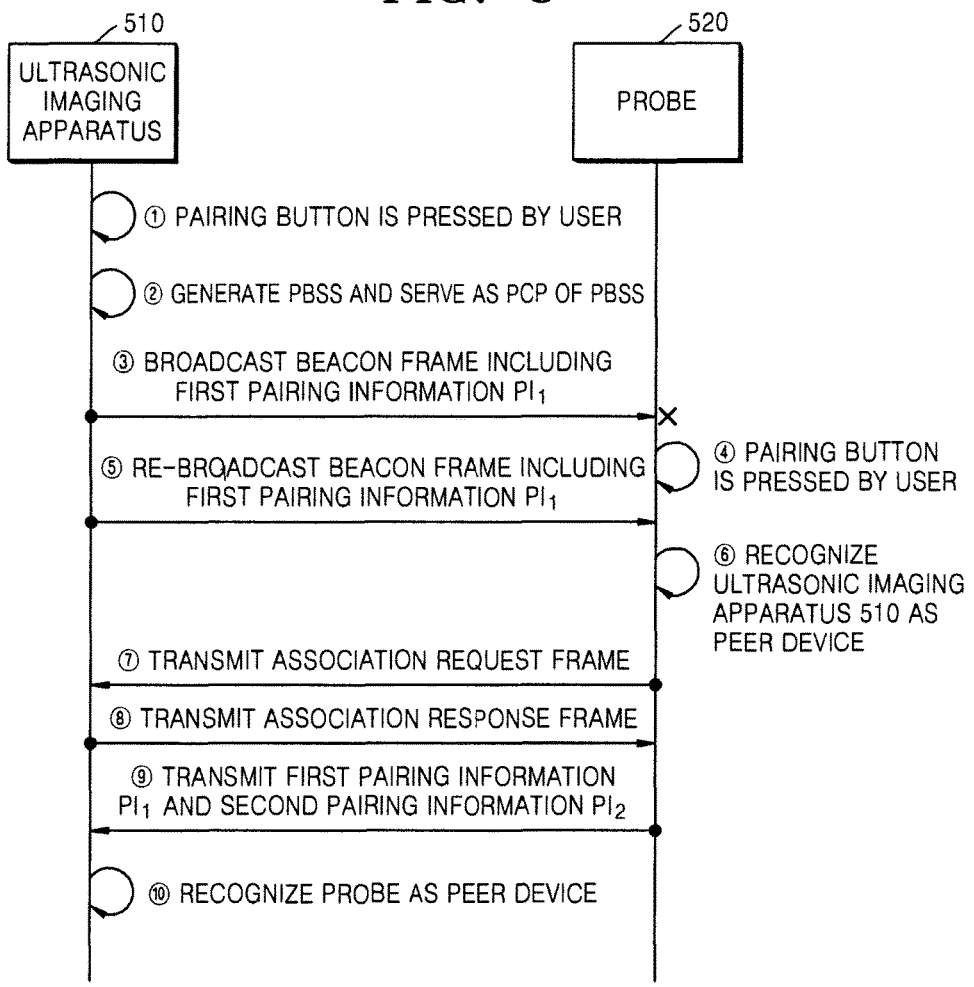
FIG. 5 is a flowchart illustrating a pairing process according to an embodiment of the present invention.

FIG. 5 is a flowchart of a pairing process according to another embodiment of the present invention where it is assumed that both an ultrasonic imaging apparatus 510 and a probe 520 are initially driven, that is, the ultrasonic imaging apparatus 510 did not yet generate any PBSSs and the probe 520 is not yet associated with any PBSSs.

In a first operation, a pairing button included in the ultrasonic imaging apparatus 510 is pressed by a user.

In a second operation, the ultrasonic imaging apparatus 510, in response to the user pressing the pairing button, generates a PBSS and becomes operational so as to serve as a PCP of the PBSS.

In a third operation, the ultrasonic imaging apparatus 510 broadcasts a beacon frame including first pairing information $PI_1$. The first pairing information $PI_1$ may include PBC information representing that the pairing button included in the ultrasonic imaging apparatus 510 has been pressed, and a MAC address of the ultrasonic imaging apparatus 510.

At this time, even when the probe 520 is turned on and is physically located at a distance capable of receiving a beacon of the ultrasonic imaging apparatus 510, the probe 520 does not parse the beacon frame but discards it because the probe 520 is not yet associated with the PBSS of the ultrasonic imaging apparatus 510. Accordingly, the probe 520 does not react to the beacon frame received in the third operation.

Although the first pairing information $PI_1$ is broadcast via the beacon frame in a beacon section in the present embodiment, the ultrasonic imaging apparatus 510 may broadcast the first pairing information $PI_1$ in a time section other than the beacon section.

In a fourth operation, a pairing button included in the probe 520 is pressed by the user. Accordingly, the probe 520 starts monitoring externally received beacon frames without discarding them.

In a fifth operation, the ultrasonic imaging apparatus 510 re-broadcasts the beacon frame including the first pairing information $PI_1$.

In a sixth operation, the probe 520 recognizes the ultrasonic imaging apparatus 510 as a peer device.

In a seventh operation, the probe 520 transmits an association request frame requesting association with the PBSS to the ultrasonic imaging apparatus 510.

In an eighth operation, the ultrasonic imaging apparatus 510 transmits to the probe 520 an association response frame approving the association request of the probe 520.

In a ninth operation, the probe 520 transmits the first pairing information $PI_1$ and second pairing information $PI_2$ to the ultrasonic imaging apparatus 510. The second pairing information $PI_2$ may include PBC information representing that the pairing button included in the probe 520 has been pressed, and a MAC address of the probe 520.

In a tenth operation, the ultrasonic imaging apparatus 510 recognizes the probe 520 as a peer device by analyzing the second pairing information $PI_2$.

Figure 6:
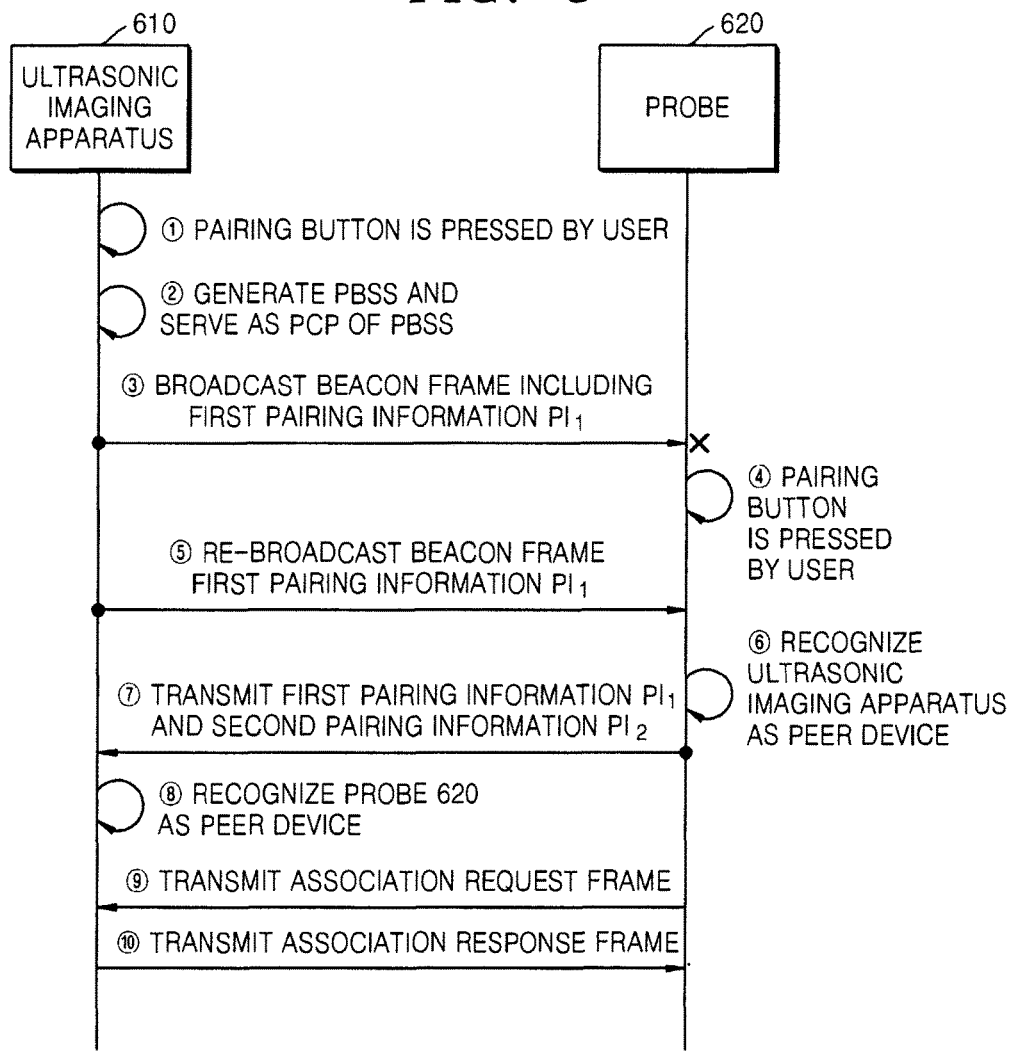
FIG. 6 is a flowchart illustrating a pairing process according to another embodiment of the present invention.

FIG. 6 is a flowchart of a pairing process according to another embodiment of the present invention where, as in the embodiment of FIG. 5, it is assumed that both an ultrasonic imaging apparatus 610 and a probe 620 are initially driven.

In a first operation, a pairing button included in the ultrasonic imaging apparatus 610 is pressed by a user.

In a second operation, the ultrasonic imaging apparatus 610 generates a PBSS and serves as a PCP of the PBSS.

In a third operation, the ultrasonic imaging apparatus 610 broadcasts a beacon frame including first pairing information $PI_1$. The first pairing information $PI_1$ may include PBC information representing that the pairing button included in the ultrasonic imaging apparatus 610 has been pressed, and a MAC address of the ultrasonic imaging apparatus 610.

At this time, even when the probe 620 is turned on and is physically located at a distance capable of receiving a beacon of the ultrasonic imaging apparatus 610, the probe 620 does not parse the beacon frame but discards it because the probe 620 is not yet associated with the PBSS of the ultrasonic imaging apparatus 610. Accordingly, the probe 620 does not react to the beacon frame received in the third operation.

In a fourth operation, a pairing button included in the probe 620 is pressed by the user. Accordingly, the probe 620 starts monitoring externally received beacon frames without discarding them.

In a fifth operation, the ultrasonic imaging apparatus 610 re-broadcasts the beacon frame including the first pairing information $PI_1$.

In a sixth operation, the probe 620 recognizes the ultrasonic imaging apparatus 610 as a peer device.

In a seventh operation, the probe 620 transmits the first pairing information $PI_1$ and second pairing information $PI_2$ to the ultrasonic imaging apparatus 610. The second pairing information $PI_2$ may include PBC information representing that the pairing button included in the probe 620 has been pressed, and a MAC address of the probe 620.

In an eighth operation, the ultrasonic imaging apparatus 610 recognizes the probe 620 as a peer device by analyzing the second pairing information $PI_2$.

In a ninth operation, the probe 620 transmits an association request frame requesting association with the PBSS to the ultrasonic imaging apparatus 610.

In a tenth operation, the ultrasonic imaging apparatus 610 transmits to the probe 620 an association response frame approving the association request of the probe 620.

As such, in the embodiment of FIG. 6, in contrast with the embodiment of FIG. 5, the probe 620 is associated with the PBSS after transmitting the second pairing information $PI_2$ to the ultrasonic imaging apparatus 610.

Figure 7:
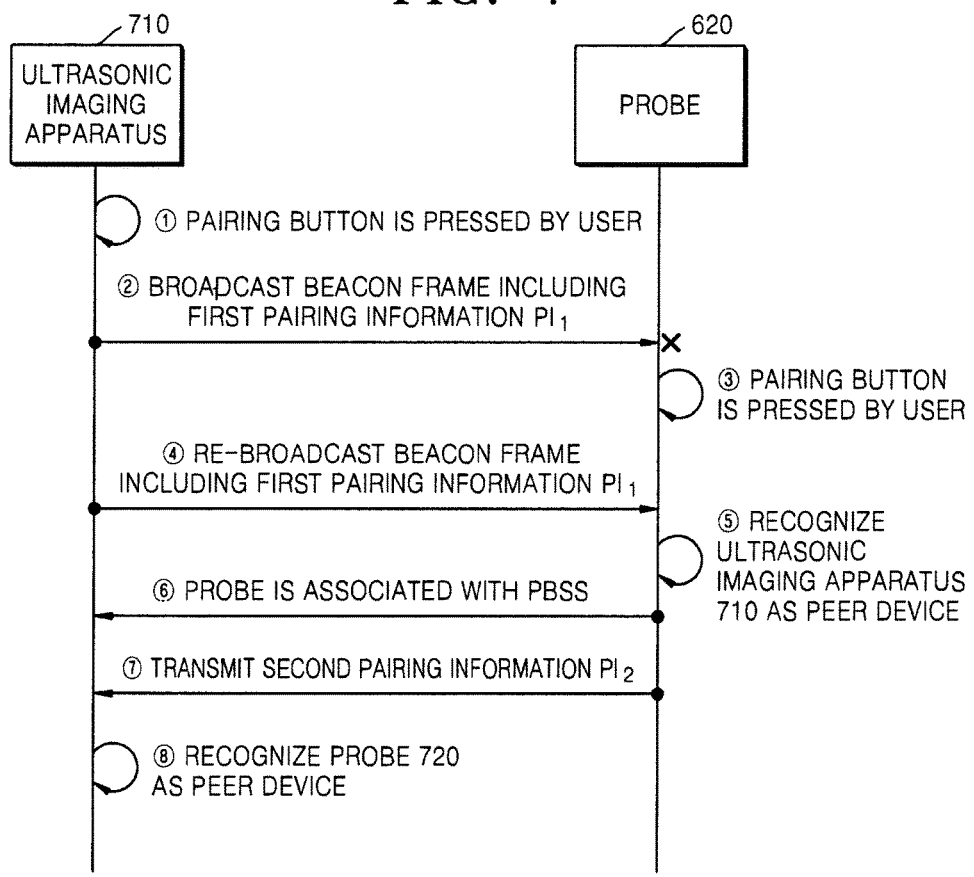
FIG. 7 is a flowchart illustrating a pairing process according to another embodiment of the present invention.

FIG. 7 is a flowchart of a pairing process according to another embodiment of the present invention where it is assumed that, while an ultrasonic imaging apparatus 710 is operating as a PCP of a PBSS, a probe 720 is initially driven.

In a first operation, a pairing button included in the ultrasonic imaging apparatus 710 is pressed by a user.

In a second operation, the ultrasonic imaging apparatus 710 broadcasts a beacon frame including first pairing information $PI_1$. The first pairing information $PI_1$ may include PBC information representing that the pairing button included in the ultrasonic imaging apparatus 710 has been pressed, and a MAC address of the ultrasonic imaging apparatus 710.

At this time, even when the probe 720 is turned on and is physically located at a distance capable of receiving a beacon frame of the ultrasonic imaging apparatus 710, the probe 720 does not parse the beacon frame but discards it because the probe 620 is not yet associated with the PBSS of the ultrasonic imaging apparatus 710. Accordingly, the probe 720 does not react to the beacon frame received in the second operation.

In a third operation, a pairing button included in the probe 720 is pressed by the user. Accordingly, the probe 720 starts monitoring externally received beacon frames without discarding them.

In a fourth operation, the ultrasonic imaging apparatus 710 re-broadcasts the beacon frame including the first pairing information $PI_1$.

In a fifth operation, the probe 720 recognizes the ultrasonic imaging apparatus 710 as a peer device.

In a sixth operation, the probe 520 is associated with the PBSS of the ultrasonic imaging apparatus 710.

In a seventh operation, the probe 520 transmits second pairing information $PI_2$ to the ultrasonic imaging apparatus 710. The second pairing information $PI_2$ may include PBC information representing that the pairing button included in the probe 720 has been pressed, and a MAC address of the probe 720.

In an eighth operation, the ultrasonic imaging apparatus 710 recognizes the probe 720 as a peer device by analyzing the second pairing information $PI_2$.

Figure 8:
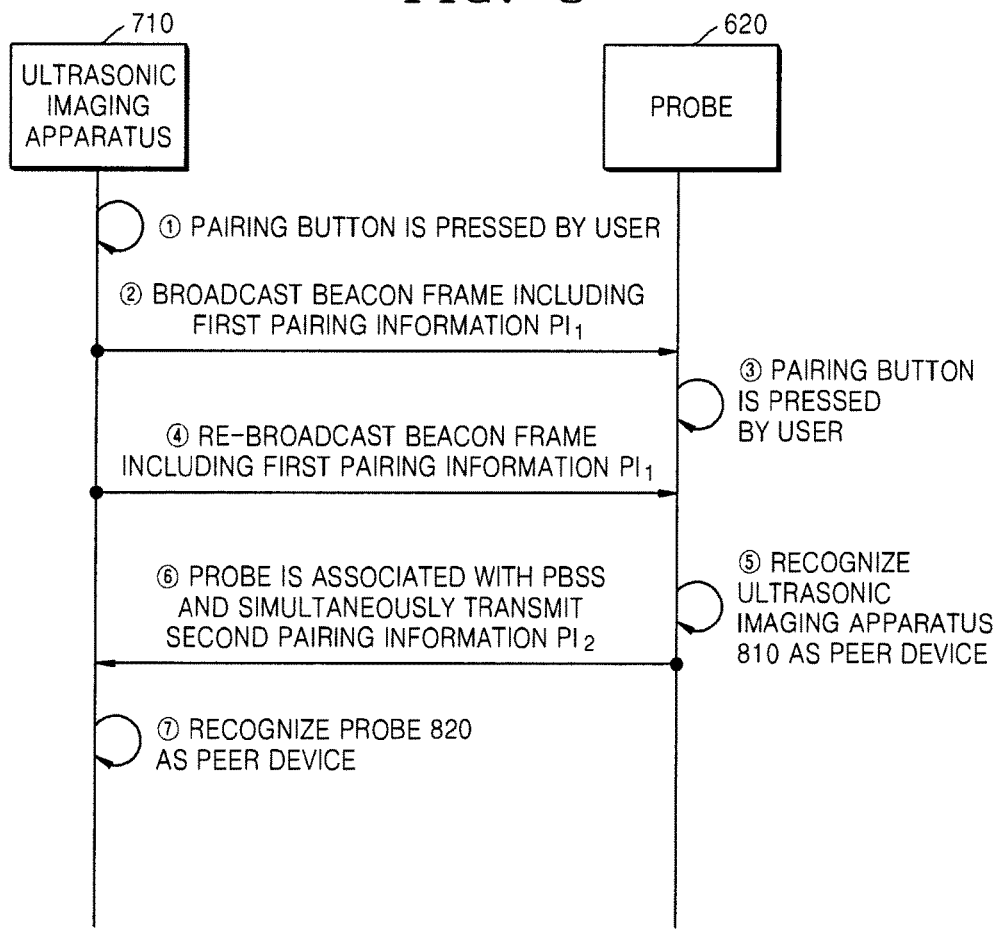
FIG. 8 is a flowchart illustrating a pairing process according to another embodiment of the present invention.

FIG. 8 is a flowchart of a pairing process according to another embodiment of the present invention where, similar to the embodiment of FIG. 7, it is assumed that while an ultrasonic imaging apparatus 810 is already operating as a PCP of a PBSS, a probe 820 is initially driven.

In a first operation, a pairing button included in the ultrasonic imaging apparatus 810 is pressed by a user.

In a second operation, the ultrasonic imaging apparatus 810 broadcasts a beacon frame including first pairing information $PI_1$. The first pairing information $PI_1$ may include PBC information representing that the pairing button included in the ultrasonic imaging apparatus 810 has been pressed, and a MAC address of the ultrasonic imaging apparatus 810.

At this time, even when the probe 820 is turned on and is physically located at a distance capable of receiving a beacon frame of the ultrasonic imaging apparatus 810, the probe 820 does not parse the beacon frame but discards it because the probe 820 is not yet associated with the PBSS of the ultrasonic imaging apparatus 810. Accordingly, the probe 820 does not react to the beacon frame received in the second operation.

In a third operation, a pairing button included in the probe 820 is pressed by the user. Accordingly, the probe 820 starts monitoring externally received beacon frames without discarding them.

In a fourth operation, the ultrasonic imaging apparatus 810 re-broadcasts the beacon frame including the first pairing information $PI_1$.

In a fifth operation, the probe 820 recognizes the ultrasonic imaging apparatus 810 as a peer device.

In a sixth operation, the probe 820 is associated with the PBSS of the ultrasonic imaging apparatus 810 and at the same time transmits second pairing information $PI_2$ to the ultrasonic imaging apparatus 810. In other words, the probe 820 carries the second pairing information $PI_2$ in an association request frame and transmits the association request frame including the second pairing information $PI_2$ to the ultrasonic imaging apparatus 810.

In a seventh operation, the ultrasonic imaging apparatus 810 recognizes the probe 820 as a peer device by analyzing the second pairing information $PI_2$.

Figure 9:
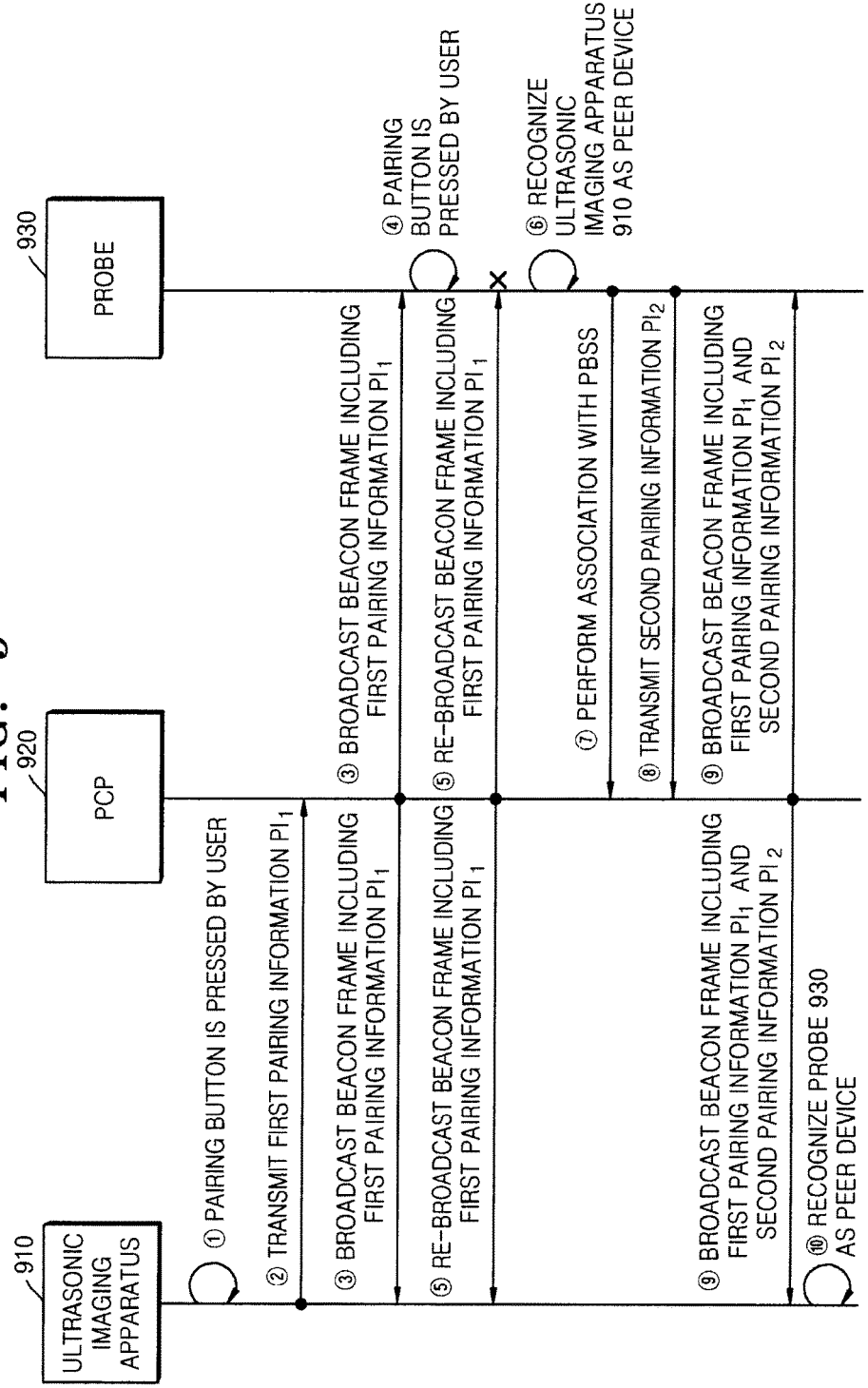
FIG. 9 is a flowchart illustrating a pairing process according to another embodiment of the present invention.

FIG. 9 is a flowchart of a pairing process according to another embodiment of the present invention. In the embodiment of FIG. 9, it is assumed that an ultrasonic imaging apparatus 910 is operating as a general station rather than a PCP 920 of a PBSS even when the ultrasonic imaging apparatus 910 already belongs to the PBSS, and that a probe 930 is initially driven.

In a first operation, a pairing button included in the ultrasonic imaging apparatus 910 is pressed by a user.

In a second operation, the ultrasonic imaging apparatus 910 transmits to a PCP 920 first pairing information $PI_1$ representing that the ultrasonic imaging apparatus 910 needs to perform pairing. The first pairing information $PI_1$ may include PBC information representing that the pairing button included in the ultrasonic imaging apparatus 910 has been pressed, and a MAC address of the ultrasonic imaging apparatus 910.

In a third operation, the PCP 920 broadcasts a beacon frame including the first pairing information $PI_1$. Since the probe 930 is not yet associated with the PBSS, the probe 930 does not parse the beacon frame but discards the same. As described above, the PCP 920 may broadcast the first pairing information $PI_1$ in a time section other than the beacon section.

In a fourth operation, a pairing button included in the probe 930 is pressed by the user. Accordingly, the probe 930 starts monitoring externally received beacon frames.

In a fifth operation, the PCP 920 re-broadcasts the beacon frame including the first pairing information $PI_1$.

In a sixth operation, the probe 930 recognizes the ultrasonic imaging apparatus 910 as a peer device of the probe 930 by referring to the first pairing information $PI_1$.

In a seventh operation, the probe 930 is associated with the PBSS of the PCP 920.

In an eighth operation, the probe 930 transmits to the PCP 920 second pairing information $PI_2$ representing that the probe 930 itself is requested by the user to perform pairing. The second pairing information $PI_2$ may be included in an association request frame that the probe 930 transmits to the PCP 920 while the probe 930 is being associated with the PBSS.

In a ninth operation, the PCP 920 broadcasts a beacon frame including the first pairing information $PI_1$ and the second pairing information $PI_2$.

In a tenth operation, in response to the beacon frame including the first pairing information $PI_1$ and the second pairing information $PI_2$, the ultrasonic imaging apparatus 910 recognizes the probe 930 as a peer device of the ultrasonic imaging apparatus 910.

As such, according to the embodiments of the present invention, pairing between an ultrasonic imaging apparatus and a probe is performed by a user simply pressing buttons included in an ultrasonic imaging apparatus and a probe. Thus the probe portion of an ultrasound imaging system may be simply and easily replaced, if necessary, while the existing ultrasonic imaging apparatus is being used.

Figure 10:
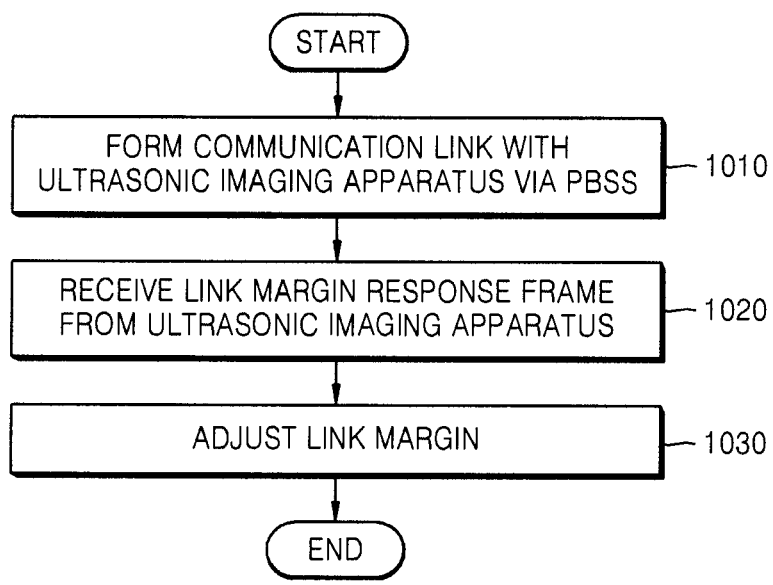
FIG. 10 is a flowchart illustrating a process of controlling a link margin, according to an embodiment of the present invention.

FIG. 10 is a flowchart of a process of controlling a link margin, according to an embodiment of the present invention.

The link margin is information used to determine a status of the communication link, and denotes a power level of a reception signal that is required by a current modulation technique. When the value of the link margin is positive, the power of the reception signal is more than necessary. When the value of the link margin is negative, the power of the reception signal is insufficient.

In operation 1010, a probe forms a communication link with an ultrasonic imaging apparatus via a PBSS. The formation of the communication link denotes completion of preparations for a communication with a peer device, including pairing.

In operation 1020, the probe receives a link margin response frame including information about the link margin (hereinafter, also referred to as link margin information) from the ultrasonic imaging apparatus, and extracts the link margin information from the link margin response frame. A format of the link margin response frame will be described later with reference to FIG. 11.

The ultrasonic imaging apparatus calculates the link margin information based on a data frame that the probe transmits in the 60 GHz band, and then informs the probe of the calculated link margin. The link margin response frame may be received every time the probe requests the link margin response frame, or may be transmitted by the ultrasonic imaging apparatus periodically without special requests or whenever the state of a link degrades.

In operation 1030, the probe adjusts the link margin based on the link margin information. To adjust the link margin, the probe may perform at least one of a change in transmission power, a change in a modulation and coding scheme (MCS), a change in beam forming, and a change in channel frequency within the 60 GHz band.

Figure 11:
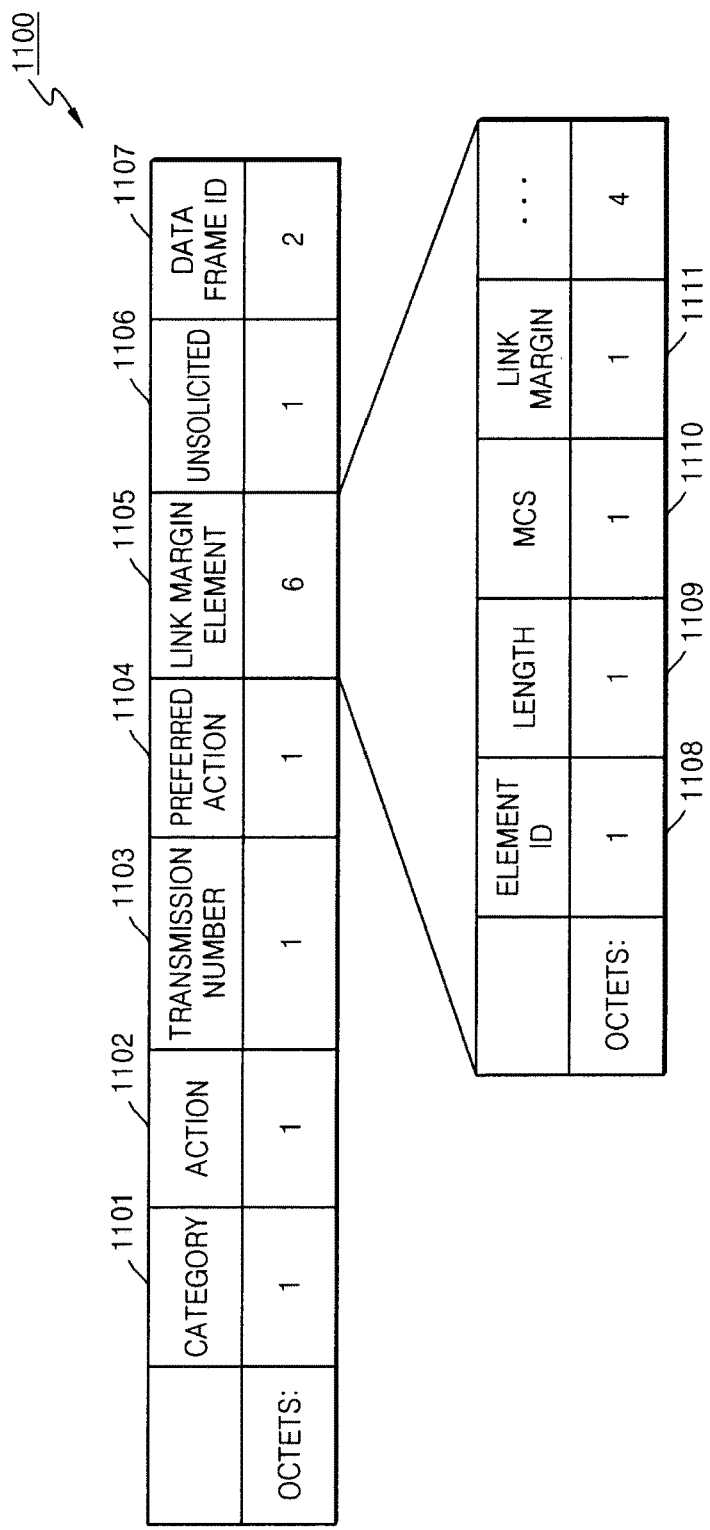
FIG. 11 illustrates a format illustrating a link margin response frame according to an embodiment of the present invention.

FIG. 11 illustrates a format of a link margin response frame 1100 according to an embodiment of the present invention.

As illustrated in FIG. 11, the link margin response frame 1100 includes a category field 1101, an action field 1102, a transmission number field 1103, a preferred action field 1104, a link margin element field 1105, an unsolicited field 1106, and a data frame ID field 1107.

The category field 1101 represents what kind of frame the link margin response frame 1100 belongs to. According to the present embodiment, the category field 1101 may indicate that the link margin response frame 1100 is a control frame.

The action field 1102 indicates that the link margin response frame 1100 is a link margin response frame categorized into a control frame which is the frame type determined by the category field 1101.

The transmission number field 1103 indicates the number of times the link margin response frame 1100 is transmitted from an ultrasonic imaging apparatus to a probe.

The preferred action field 1104 indicates one operation that the ultrasonic imaging apparatus requests from among a change in transmission power, a change in MCS, beam forming, and a channel frequency change. When the link margin response frame 1100 including the preferred action field 1104 is received, the probe may perform the operation indicated by the preferred action field 1104 or may perform an operation for margin adjustment independently without respect to the preferred action field 1104. Although the preferred action field 1104 is illustrated as an independent field of the link margin response frame 1100 in FIG. 11, the preferred action field 1104 may be a subfield of the link margin element field 1105.

The link margin element field 1105 includes the link margin information and is divided into an element ID field 1108, a length field 1109, a MCS field 1110, and a link margin field 1111.

The element ID field 1108 indicates that the link margin element field 1105 is a field including the link margin information.

The length field 1109 indicates a length of the link margin element field 1105.

The MCS field 1110 indicates an index representing an MCS which is to be changed, when the preferred action field 1104 indicates that the ultrasonic imaging apparatus requests a change in the MCS.

The link margin field 1111 records information about the link margin calculated by the ultrasonic imaging apparatus.

The unsolicited field 1106 represents whether the link margin response frame 1100 is received in response to a request frame of the probe. For example, when the link margin response frame 1100 is received in response to a request of the probe, the unsolicited field 1106 may record 0, and otherwise, the unsolicited field 1106 may record a value other than 0. If the probe transmits a link margin request frame (not shown) to the ultrasonic imaging apparatus to request the link margin response frame 1100, the link margin request frame may include at least one of a category field indicating the kind of frame, an action field indicating that the link margin response frame 1100 is a link margin request frame from among frames categorized into the kind of frame indicated by the category field, and a transmission number field representing the number of times the link margin request frame is transmitted.

The data frame ID field 1107 includes a sequence number of a data frame used when the ultrasonic imaging apparatus calculates the link margin. Through these pieces of information, the probe can recognize a time for calculating the link margin, and thus may adequately control the state of a communication link.

Figure 12:
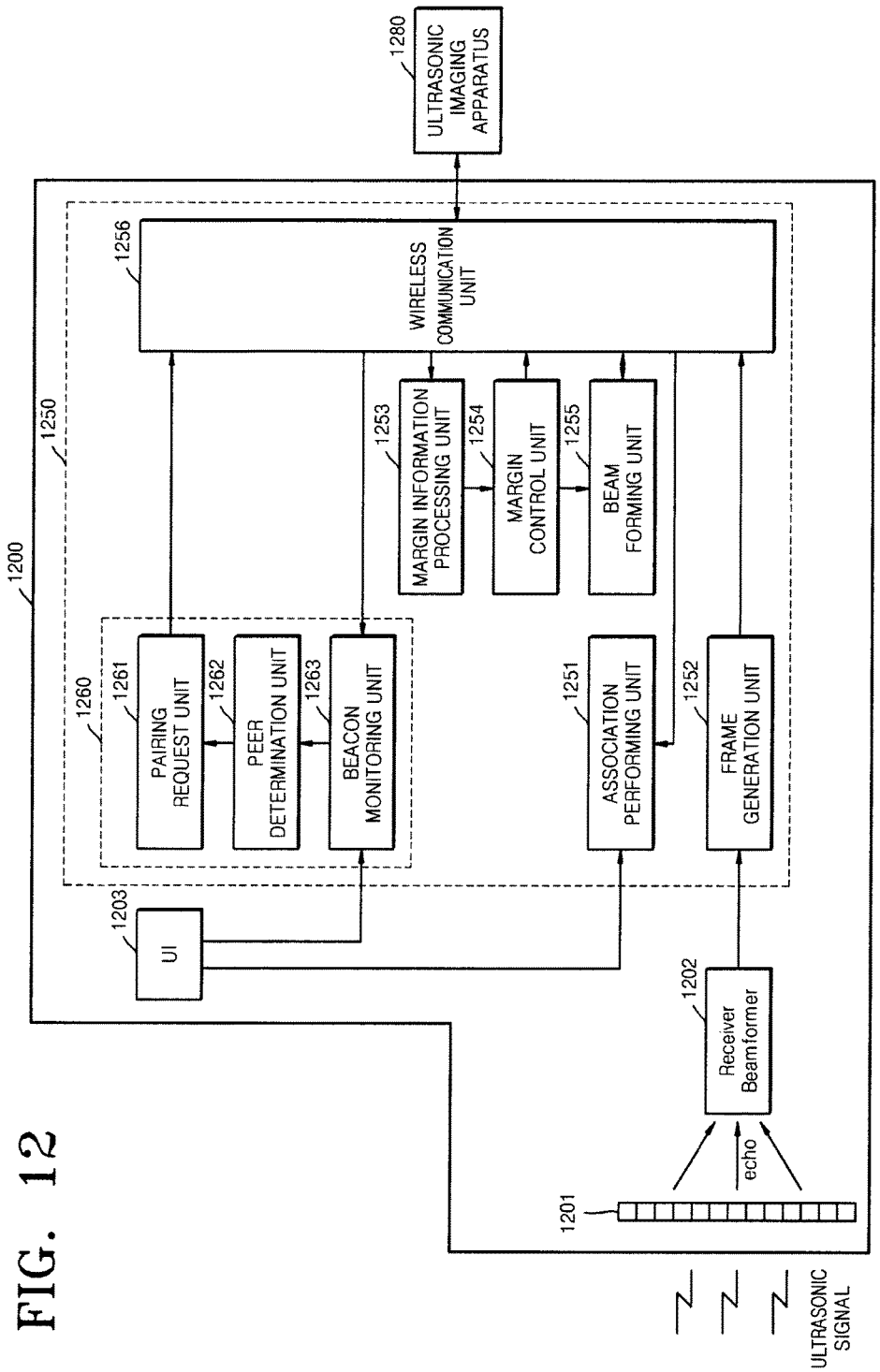
FIG. 12 is a block diagram illustrating a structure of a probe apparatus according to an embodiment of the present invention.

FIG. 12 is a block diagram of a structure of a probe apparatus 1200 according to another embodiment of the present invention.

As illustrated in FIG. 12, the probe apparatus 1200 includes a transducer 1201, a receiver beam former 1202, a user interface 1203, and a wireless transceiver module 1250.

The wireless transceiver module 1250 includes an association performing unit 1251, a frame generation unit 1252, a margin information processing unit 1253, a margin control unit 1254, a beam forming unit 1255, a wireless communication unit 1256, and a link formation unit 1260. The link formation unit 1260 includes a pairing request unit 1261, a peer determination unit 1262, and a beacon monitoring unit 1263. The wireless transceiver module 1250 may further include other various components such as a battery, an analog to digital converter (ADC), and a low noise amplifier (LNA). This will be apparent to one of ordinary skill in the art, thus no further descriptions thereof are provided.

The transducer 1201 converts an ultrasonic echo signal received from a test target into an electrical signal, and the receiver beam former 1202 gathers multiple channels of echo signals (more specifically, digital data into which the echo signals are converted) received from oscillators arranged in an array or matrix form in the transducer 1201.

The wireless transceiver module 1250 performs procedures necessary for transmitting an echo signal to an ultrasonic imaging apparatus 1280 in the 60 GHz frequency band. The association performing unit 1251 performs a procedure for associating the probe apparatus 1200 using a mmWave-based wireless network. As described above, the mmWave-based wireless network may be a PBSS that follows the WiGig standard of WGA. When the probe 1200 and the ultrasonic imaging apparatus 1280 perform communications via the PBSS, the ultrasonic imaging apparatus 1280 may operate as a PCP instead of the probe 1200, in order that the size and weight of the probe 1200 can be kept low by not including the components therein which would be necessary to allow the probe to be a PCP.

The frame generation unit 1252 generates a data frame with a format suitable for the mmWave-based wireless network, by using the echo signal received via the transducer 1201.

The wireless communication unit 1256 transmits the data frame generated by the frame generation unit 1252 to the ultrasonic imaging apparatus 1280 via the 60 GHz frequency band.

The beam forming unit 1255 performs mmWave beamforming together with the ultrasonic imaging apparatus 1280. In other words, the beam forming unit 1255 performs procedures necessary for efficiently transmitting and receiving data to and from the ultrasonic imaging apparatus 1280 by using mmWaves, such as by using sector level sweeping and beam refinement techniques, well known to those of ordinary skill in the art.

The link formation unit 1260 forms a link with the ultrasonic imaging apparatus 1280. When a user command for making a pairing request is received via the user interface 1203, the beacon monitoring unit 1263 receives a mmWave beacon of the PBSS to which the ultrasonic imaging apparatus 1280 belongs. The reception of the user command for making a pairing request denotes not only physical reception but also requests an operation of parsing and analyzing a received beacon frame.

Accordingly, the peer determination unit 1262 detects the ultrasonic imaging apparatus 1280 which is to be paired with the probe 1200 by using first pairing information included in the mmWave beacon. The first pairing information represents that the ultrasonic imaging apparatus 1280 has been requested by a user to perform pairing, and may include the MAC address of the ultrasonic imaging apparatus 1280 and PBC information representing that a PBC-type pairing button included in the ultrasonic imaging apparatus 1280 has been pressed.

The pairing request unit 1261 transmits second pairing information representing that the probe 1200 requests pairing, to the ultrasonic imaging apparatus 1280 via the PBSS. The second pairing information may include the MAC address of the probe 1200 and PBC information representing that a PBC-type pairing button included in the probe 1200 has been pressed.

The margin information processing unit 1253 extracts information about a link margin of a communication link from the ultrasonic imaging apparatus 1280. The link margin information may be included in a link margin response frame that the ultrasonic imaging apparatus 1280 transmits to the probe 1200 in response to a request of the probe 1200 or periodically without requests or when the state of the communication link degrades.

The margin control unit 1254 controls the link margin based on the link margin response frame. More specifically, the margin control unit 1254 may adjust the link margin by performing at least one of a change in transmission power, a change in a MCS, a change in beam forming, and a change in a channel frequency within the 60 GHz frequency band.

The above-described method and apparatus embodiments of the present invention can be realized in hardware or as software or computer code that can be stored in a recording medium such as a CD ROM, an RAM, a floppy disk, a hard disk, a DVD or a magneto-optical disk or downloaded over a network, so that the methods described herein can be rendered in such software using a general purpose computer, or a special processor or in programmable or dedicated hardware, such as an ASIC or FPGA. As would be understood in the art, the computer, the processor or the programmable hardware include memory components, e.g., RAM, ROM, Flash, etc. that may store or receive software or computer code that when accessed and executed by the computer, processor or hardware implement the processing methods described herein.

While the present invention has been particularly shown and described with reference to exemplary embodiments thereof, it will be understood by those of ordinary skill in the art that various changes in form and details may be made therein without departing from the spirit and scope of the present invention as defined by the following claims and their equivalents.

What is claimed is:

1. A probe apparatus for ultrasound diagnostic imaging, comprising:
a memory storing instructions; and
a processor configured to execute the stored instructions to:
perform a procedure for associating the probe apparatus with an ultrasonic imaging apparatus, by pairing the probe apparatus with the ultrasonic imaging apparatus through an external device functioning as a Personal Basic Service Set (PBSS) control point (PCP), using beacon signals received from the external device, thereby forming a communication link between the probe apparatus and the ultrasonic imaging apparatus, the procedure being consistent with an IEEE 802.11ad standard;
generate a data frame with a format suitable for the IEEE 802.11ad standard, by using an echo signal received via a transducer; and
transmit the data frame to the ultrasonic imaging apparatus using a signal channel in a 60 GHz frequency band consistent with the IEEE 802.11ad standard,
wherein the procedure for associating the probe apparatus with the ultrasonic imaging apparatus is performed by receiving a first pairing information included within the beacon signals and consistent with the IEEE 802.11ad standard which represents that the ultrasonic imaging apparatus has been requested by a user to perform pairing via input through a pairing button at the ultrasonic imaging apparatus, and transmitting a second pairing information consistent with the IEEE 802.11ad standard which represents that the probe apparatus has been requested by the user to perform pairing via input through a pairing button at the probe apparatus.

2. The probe apparatus of claim 1, the processor is further configured to perform mmWave beamforming of the signal in the 60 GHz frequency band in order to transmit the data frame to the ultrasonic imaging apparatus.

3. A probe apparatus for ultrasound diagnostic imaging, the probe apparatus comprising:
a memory storing instructions; and
a processor configured to execute the stored instructions to:
monitor for reception of a mmWave beacon from an external device functioning as a Personal Basic Service Set (PBSS) control point (PCP), when the probe apparatus is not yet associated with an ultrasonic imaging apparatus, and a user command for making a pairing request is received;
detect the ultrasonic imaging apparatus which is to be paired with the probe apparatus by using first pairing information included in the received mmWave beacon;
perform a procedure for associating the probe apparatus with the ultrasonic imaging apparatus by using a basic service set ID (BSSID) included in the received mmWave beacon;
transmit second pairing information to the ultrasonic imaging apparatus via the PBSS, by pairing the probe apparatus with an ultrasonic imaging apparatus through the external device, thereby enabling the pairing between the ultrasonic imaging apparatus and the probe apparatus and formation of a communication link in a mmWave band therebetween;
wherein the first pairing information represents that the ultrasonic imaging apparatus has been requested by a user to perform pairing, and the second pairing information represents that the probe apparatus has been requested by the user to perform pairing via input through a pairing button at the probe apparatus, and the first pairing information comprises push button configuration (PBC) information representing that a pairing button for requesting pairing by using a PBC technique has been pressed in the ultrasonic imaging apparatus.

4. The probe apparatus of claim 3, wherein the first pairing information comprises a medium access control (MAC) address of the ultrasonic imaging apparatus, and the second pairing information comprises a MAC address of the probe apparatus and PBC information representing that the pairing button for requesting pairing by using the PBC technique has been pressed in the probe apparatus.

5. The probe apparatus of claim 3, wherein the processor is further configured to transmit an echo signal received via a transducer portion of the probe apparatus, to the ultrasonic imaging apparatus via a signal channel in a 60 GHz frequency band via the PBSS of the ultrasonic imaging apparatus.

6. The probe apparatus of claim 3, wherein the processor is further configured to perform beamforming of the mmWave beacon transmitted to the ultrasonic imaging apparatus.

7. A probe apparatus for ultrasound diagnostic imaging, comprising:
a memory storing instructions; and
a processor configured to execute the stored instructions to:
form a communication link with an ultrasonic imaging apparatus in a Personal Basic Service Set (PBSS) that uses mmWaves;
extract information about a link margin of the communication link from a link margin response frame received from the ultrasonic imaging apparatus; and control the probe apparatus to perform, based on the extracted information about a link margin, a change in channel frequency within a 60 GHz frequency band and a selected one of a change in transmission power of an echo signal, a change in a modulation and coding scheme (MCS) to be applied to the echo signal, and a change in beam forming with the ultrasonic imaging apparatus, wherein the communication link is formed by receiving a first pairing information consistent with an IEEE 802.11ad standard included within beacon signals from the ultrasonic imaging apparatus which represents that the ultrasonic imaging apparatus has been requested by a user to perform pairing via input through a pairing button at the ultrasonic imaging apparatus, and transmitting a second pairing information consistent with the IEEE 802.11ad standard which represents that the probe apparatus has been requested by the user to perform pairing via input through a pairing button at the probe apparatus.

8. The probe apparatus of claim 7, wherein the processor transmits a link margin request frame requesting information about the link margin to the ultrasonic imaging apparatus, and the link margin response frame is received in response to the link margin request frame.

9. The probe apparatus of claim 8, wherein the link margin request frame comprises at least one of a category field indicating what kind of frame the link margin request frame belongs to, an action field indicating that the link margin request frame is a link margin request frame from among frames categorized into the kind of frame determined by the category field, and a transmission number field representing the number of times the link margin request frame is transmitted.

10. The probe apparatus of claim 7, wherein the link margin response frame comprises a preferred action field that comprises information that indicates a request for one operation from among the change in the transmission power, the change in the MCS, a change in the beam forming, and the change in channel frequency, to be performed.

11. A communication method of a probe apparatus for ultrasound diagnostic imaging, the communication method comprising:
performing a procedure for associating the probe apparatus with an ultrasonic imaging apparatus, by pairing the probe apparatus with an ultrasonic imaging apparatus through an external device functioning as a Personal Basic Service Set (PBSS) control point (PCP), using beacon signals received from the external device, thereby forming a communication link between the probe apparatus and the ultrasonic imaging apparatus, the procedure being consistent with an IEEE 802.11ad standard;
generating a data frame with a format suitable for a mmWave-based wireless network, by using an echo signal received via an ultrasound transducer portion of the probe apparatus; and
transmitting the data frame to the ultrasonic imaging apparatus using a signal channel in a 60 GHz frequency band consistent with the IEEE 802.11ad standard,
wherein the procedure for associating the probe apparatus with the ultrasonic imaging apparatus is performed by receiving a first pairing information included within the beacon signals and consistent with the IEEE 802.11ad standard which represents that the ultrasonic imaging apparatus has been requested by a user to perform pairing via input through a pairing button at the ultrasonic imaging apparatus, and transmitting a second pairing information consistent with the IEEE 802.11ad standard which represents that the probe apparatus has been requested by the user to perform pairing via input through a pairing button at the probe apparatus.

12. The communication method of claim 11, further comprising performing beamforming of a mmWave beacon transmitted to the ultrasonic imaging apparatus.

13. A communication method of a probe apparatus for ultrasound diagnostic imaging, the communication method comprising:
receiving a mmWave beacon from an external device functioning as a Personal Basic Service Set (PBSS) control point (PCP), when the probe apparatus is not yet associated with an ultrasonic imaging apparatus, and a user command for making a pairing request is received;
detecting the ultrasonic imaging apparatus which is to be paired with the probe apparatus by using first pairing information included in the received mmWave beacon;
performing a procedure for associating the probe apparatus with a PBSS of the ultrasonic imaging apparatus by using a basic service set ID (BSSID) included in the received mmWave beacon; and
transmitting second pairing information to the ultrasonic imaging apparatus via the PBSS, by pairing the probe apparatus with an ultrasonic imaging apparatus through the external device, thereby enabling the pairing between the ultrasonic imaging apparatus and the probe apparatus and formation of a communication link in a mmWave band therebetween;
wherein the first pairing information represents that the ultrasonic imaging apparatus has been requested by a user to perform pairing, and the second pairing information represents that the probe apparatus has been requested by the user to perform pairing via input through a pairing button at the probe apparatus, and the first pairing information comprises push button configuration (PBC) information representing that a pairing button for requesting pairing by using a PBC technique has been pressed in the ultrasonic imaging apparatus.

14. The communication method of claim 13, wherein the first pairing information comprises a medium access control (MAC) address of the ultrasonic imaging apparatus, and the second pairing information comprises a MAC address of the probe apparatus and PBC information representing that a button for requesting pairing by using the PBC technique has been pressed in the probe apparatus.

15. The communication method of claim 13, further comprising transmitting an echo signal received via an ultrasound transducer portion of the probe to the ultrasonic imaging apparatus, using a signal channel in a 60 GHz frequency band via the PBSS of the ultrasonic imaging apparatus.

16. The communication method of claim 13, further comprising performing beamforming of the mmWave beacon transmitted to the ultrasonic imaging apparatus.

17. A communication method of a probe apparatus for ultrasound diagnostic imaging, the communication method comprising:
forming a communication link with an ultrasonic imaging apparatus in a Personal Basic Service Set (PBSS) that uses mmWaves for signal transmission;
extracting information about a link margin of the communication link from a link margin response frame received from the ultrasonic imaging apparatus; and performing, based on the extracted information about a link margin, a change in channel frequency within a 60 GHz frequency band and a selected one of a change in transmission power of an echo signal, a change in a modulation and coding scheme (MCS) to be applied to the echo signal, a change in beam forming with the ultrasonic imaging apparatus, wherein the communication link is formed by receiving a first pairing information consistent with an IEEE 802.11ad standard included within beacon signals from the ultrasonic imaging apparatus which represents that the ultrasonic imaging apparatus has been requested by a user to perform pairing via input through a pairing button at the ultrasonic imaging apparatus, and transmitting a second pairing information consistent with the IEEE 802.11ad standard which represents that the probe apparatus has been requested by the user to perform pairing via input through a pairing button at the probe apparatus.

18. The communication method of claim 17, further comprising transmitting to the ultrasonic imaging apparatus a link margin request frame requesting the information about the link margin, wherein the link margin response frame is received in response to transmission of the link margin request frame.

19. The communication method of claim 18, wherein the link margin request frame comprises at least one of a category field indicating what kind of frame the link margin request frame belongs to, an action field indicating that the link margin request frame is a link margin request frame from among frames categorized into the kind of frame determined by the category field, and a transmission number field representing the number of times the link margin request frame is transmitted.

20. The communication method of claim 17, wherein the link margin response frame comprises a preferred action field that comprises information that indicates a request for one operation from among the change in the transmission power, the change in the MCS, the change in beam forming, and the change in channel frequency, to be performed.

21. An ultrasound diagnostic system comprising:
a probe apparatus configured to become associated with an ultrasonic imaging apparatus, thereby forming a communication link therebetween, using a procedure consistent with an IEEE 802.11ad standard, the probe apparatus further configured to: transmit an echo signal received via a transducer portion of the probe apparatus to the ultrasonic imaging apparatus using a signal channel in a 60 GHz frequency band consistent with the IEEE 802.11ad standard;
the ultrasonic imaging apparatus configured to generate an ultrasonic image by using the echo signal received in the 60 GHz frequency band consistent with the IEEE 802.11ad standard; and
a device communicatively coupled to both the probe apparatus and the imaging apparatus, configured to operate as a Personal Basic Service Set (PBSS) control point (PCP), wherein the device transmits a beacon signal to each of the probe apparatus and the ultrasonic imaging apparatus so that pairing between the probe apparatus and the ultrasonic imaging apparatus is performed through the device, wherein the probe apparatus is configured to become associated with the ultrasonic imaging apparatus by receiving a first pairing information included in the beacon signal transmitted by the device, consistent with the IEEE 802.11ad standard which represents that the ultrasonic imaging apparatus has been requested by a user to perform pairing via input through a pairing button at the ultrasonic imaging apparatus, and transmitting a second pairing information consistent with the IEEE 802.11ad standard which represents that the probe apparatus has been requested by the user to perform pairing via input through a pairing button at the probe apparatus.

22. A probe apparatus for ultrasound diagnostic imaging, comprising:
a memory storing instructions; and
a processor configured to execute the stored instructions to:
perform a procedure for associating the probe apparatus with an ultrasonic imaging apparatus consistent with an IEEE 802.11ad standard by pairing the probe apparatus with an ultrasonic imaging apparatus and thereby forming a communication link there between, through an external device functioning as a Personal Basic Service Set (PBSS) control point (PCP);
extract information about a link margin of the communication link from a link margin response frame received from the ultrasonic imaging apparatus;
implement, based on the extracted information about the link margin, a change in at least a channel frequency within a 60 GHz frequency band;
generate a data frame with a format suitable for the IEEE 802.11ad standard, by using an echo signal received via a transducer; and
transmit the data frame to the ultrasonic imaging apparatus using a signal channel in a 60 GHz frequency band consistent with the IEEE 802.11ad standard, wherein the procedure for associating the probe apparatus with the ultrasonic imaging apparatus is performed by receiving a first pairing information consistent with the IEEE 802.11ad standard from the ultrasonic imaging apparatus which represents that the ultrasonic imaging apparatus has been requested by a user to perform pairing via input through a pairing button at the ultrasonic imaging apparatus, and transmitting a second pairing information consistent with the IEEE 802.11ad standard which represents that the probe apparatus has been requested by the user to perform pairing via input through a pairing button at the probe apparatus.

* * * * *

UNITED STATES PATENT AND TRADEMARK OFFICE
CERTIFICATE OF CORRECTION

PATENT NO. : 10,129,926 B2
APPLICATION NO. : 13/495364
DATED : November 13, 2018
INVENTOR(S) : Kim et al.

Page 1 of 1

It is certified that error appears in the above-identified patent and that said Letters Patent is hereby corrected as shown below:

In the Claims

Column 18, Claim 22, Line 28 should read as follows:
--...link therebetween, through an...--

Signed and Sealed this
Eleventh Day of December, 2018

Andrei Iancu
*Director of the United States Patent and Trademark Office*